United States Patent
Heiries et al.

(10) Patent No.: US 9,594,108 B2
(45) Date of Patent: Mar. 14, 2017

(54) METHOD AND SYSTEM FOR PROTECTING AGAINST ELECTRICAL ARCS IMPLEMENTING A MODULATION SPECIFIC TO A MODULE OF THE ACOUSTIC WAVE ACCOMPANYING AN ELECTRICAL ARC

(71) Applicant: COMMISSARIAT A L'ENERGIE ATOMIQUE ET AUX ENE ALT, Paris (FR)

(72) Inventors: Vincent Heiries, Saint-Jean de Moirans (FR); Jean-Louis Lacoume, Gieres (FR); Pierre Perichon, Voiron (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 47 days.

(21) Appl. No.: 14/584,283

(22) Filed: Dec. 29, 2014

(65) Prior Publication Data
US 2015/0198650 A1    Jul. 16, 2015

(30) Foreign Application Priority Data
Jan. 15, 2014   (FR) ..................... 14 50316

(51) Int. Cl.
*G01R 31/08* (2006.01)
*G01N 29/00* (2006.01)
(Continued)

(52) U.S. Cl.
CPC ............. *G01R 31/08* (2013.01); *G01N 29/00* (2013.01); *G01R 31/10* (2013.01); *G01R 31/1209* (2013.01)

(58) Field of Classification Search
CPC ......... G01R 31/333; H01H 9/50; H01H 33/26
(Continued)

(56) References Cited

U.S. PATENT DOCUMENTS

| 4,291,204 A | 9/1981 | Crick |
| 7,710,253 B1 * | 5/2010 | Fredricks ........... H05B 33/0884 315/76 |

(Continued)

FOREIGN PATENT DOCUMENTS

DE    10 2011 009 512 A1    7/2012

OTHER PUBLICATIONS

French Preliminary Search Report issued Sep. 29, 2014, in French Application No. 14 50316 filed Jan. 15, 2014 (with English Translation of Categories of Cited Documents).

*Primary Examiner* — Patrick Assouad
*Assistant Examiner* — Demetrius Pretlow
(74) *Attorney, Agent, or Firm* — Oblon, McClelland, Maier & Neustadt, L.L.P.

(57) ABSTRACT

The invention relates to an electrical system comprising a plurality of modules that can be powered independently withy current, characterized in that it further comprises:
 a module configured to apply to each of the modules a current which is modulated by a signal specific to the module,
 an acoustic sensor enabling the measurement of an acoustic signal that accompanies an electrical arc generated by a defective module,
 a treatment unit configured to identify a signature of one of the specific signals in the acoustic signal measured by the acoustic sensor in order to identify the defective module.

The invention also relates to a method for locating faults in such an electrical system.

10 Claims, 2 Drawing Sheets

(51) Int. Cl.
*G01R 31/10* (2006.01)
*G01R 31/12* (2006.01)

(58) Field of Classification Search
USPC ................................. 324/512–536, 645–648
See application file for complete search history.

(56) References Cited

U.S. PATENT DOCUMENTS

| | | | |
|---|---|---|---|
| 8,570,017 | B2 | 10/2013 | Perichon et al. |
| 9,158,023 | B2* | 10/2015 | Stephan .................... G01V 3/10 |
| 2002/0130668 | A1* | 9/2002 | Blades ..................... G01R 1/07 |
| | | | 324/536 |
| 2003/0145263 | A1* | 7/2003 | Song ................ G01R 31/31707 |
| | | | 714/726 |
| 2005/0013075 | A1* | 1/2005 | Köhlmeier-Beckmann H02J 13/0024 |
| | | | 361/62 |
| 2010/0321838 | A1* | 12/2010 | Wu ...................... H02H 1/0023 |
| | | | 361/42 |
| 2011/0012603 | A1* | 1/2011 | Bose .................. G01R 31/3274 |
| | | | 324/418 |
| 2011/0121969 | A1* | 5/2011 | Mercer .................. A61B 6/581 |
| | | | 340/540 |
| 2011/0267721 | A1* | 11/2011 | Chaintreuil ........ G01R 31/1209 |
| | | | 361/2 |
| 2012/0006117 | A1 | 1/2012 | Kordon et al. |
| 2012/0095706 | A1* | 4/2012 | Zhou .................... H02H 1/0023 |
| | | | 702/58 |
| 2012/0327745 | A1 | 12/2012 | Yardibi et al. |
| 2014/0070833 | A1* | 3/2014 | Luebke ................... H02S 50/10 |
| | | | 324/754.21 |
| 2014/0218044 | A1* | 8/2014 | Ostrovsky ............ G01R 31/025 |
| | | | 324/509 |
| 2015/0160284 | A1* | 6/2015 | Cern .................. G01R 31/1272 |
| | | | 324/536 |

* cited by examiner

METHOD AND SYSTEM FOR PROTECTING AGAINST ELECTRICAL ARCS IMPLEMENTING A MODULATION SPECIFIC TO A MODULE OF THE ACOUSTIC WAVE ACCOMPANYING AN ELECTRICAL ARC

TECHNICAL FIELD

The field of the invention is that of electrical systems, in particular high voltage, inside of which electrical arcs can occur: electrical cabinets, transformers, wiring, batteries.

The invention relates more particularly to a technique for detecting and for locating electrical arcs based on a measurement of the acoustic wave generated by an electrical arc.

PRIOR ART

In electrical systems, the breaking of a cable or a defective connector can result in an electrical arc which, if it is maintained, will cause degradations. In the case of systems operating in direct current, such as batteries for example, the electrical arc formed is maintained and can be at the origin of substantial heating leading to the start of a fire.

The early detection of an electrical arc is as such a major stake for the operating safety of electrical systems, and of batteries in particular.

A generic method for detecting arcs is based on measurements of current and of voltage which are disturbed by the appearance of an electrical arc. Via a suitable treatment of these measurements, it is possible to detect the appearance of the electrical arc. This solution however cannot be applied for certain applications, as for example batteries wherein the electrochemical storage means have very low impedance which weakens the voltage signature of the electrical arcs. In order to overcome this problem of detection, a large number of sensors would have to be used, which would induce an unsuitable cost.

Another method for detecting arcs is based on measuring the optical radiation. This solution cannot however be applied in applications where the radiation sensor is unable to detect the radiation of certain connections that are concealed by a protective case of complex shape or are arranged at the core of a module and concealed by other components.

Another method for detecting arcs, used in photovoltaic panels, is based on measuring the electromagnetic field and identifying a specific signature. Such detection induces a substantial number of false alarms in particular when the surrounding electromagnetic noise is substantial. Moreover, such a detection is highly affected by any screen to the propagation of the electromagnetic waves. Furthermore, such a detection has a relatively long response time.

Another method for detecting electrical arcs is based on detecting the acoustic wave which manifests itself in the presence of an electrical arc. It is as such known in patent application US 2012/0006117 A1 a technique consisting in applying an electric signal in a buried electric cable. This signal will generate an electrical arc at the level of a cable fault, with this electrical arc triggering a discharge noise in the form of an acoustic signal. This acoustic signal is detected on the surface and makes it possible to locate the defect.

Also known in application U.S. Patent 2012/327745 A1 is a system for monitoring breakdowns in an electric substation using a set of acoustic sensors and wherein the acoustic signals measured are compared with signatures that are characteristic of breakdowns. And from application DE 10 2011 009512 A1 is known a method for locating a defect by the generating of an electrical discharge on the fault by means of a combination of a high voltage pulse and of a low voltage pulse, and through the acoustic detection of the discharge The electrical systems are often broken down into a plurality of modules, with each module able to be defective and generate an electrical arc. By module is meant a sub-assembly of an electrical system, for example a particular piece of electrical equipment, a cable, a connector, a cell, or a group of such elements.

Although the methods of detection shown hereinabove make it possible to detect an electrical arc generated in an electrical system, they do not make it possible to identify the defective module where the electrical arc is originating from. Yet such an identification is desirable, in particular for the purposes of maintenance or in order to isolate the defective module while continuing to supply the other modules of the system in order to provide service continuity for it.

DESCRIPTION OF THE INVENTION

The invention aims to overcome this problem of identifying a defective module where an electrical arc originates from in an electrical system broken down into a plurality of modules. For this it proposes a method for locating faults in an electrical system comprising a plurality of modules that can be supplied independently with current, characterised in that it comprises the following steps:
  application to each of the modules of a current which is modulated by a signal that is specific to the module,
  measurement of an acoustic signal that accompanies an electrical arc generated by a defective module,
  identification of a signature of one of the specific signals in the measured acoustic signal in order to identify the defective module.

Certain preferred but not limited aspects of this method are the following:
  identifying a signature of one of the specific signals in the measured acoustic signal comprises a correlation of the measured acoustic signal with each one of the specific signals;
  identifying the defective module comprises the identification of an auto-correlation peak among the correlation results of the measured acoustic signal with each of the specific signals;
  it further comprises a step of locating the electrical arc by determining, using the auto-correlation results of the measured acoustic signal with the specific signal associated with the defective module, of the propagation time of the acoustic wave from the electrical arc to an acoustic sensor taking the measurement of the acoustic signal;
  it includes determining the propagation time of the acoustic wave from the electrical arc to at least three acoustic sensors taking the measurement of the acoustic signal, and a triangulation of the propagation times determined as such.
  a specific signal to a module is a sequence of pseudo-random code, for example a Gold code or a Kasami code.
  each one of the specific signals is formatted by a rectangular waveform before correlation with the measured acoustic signal.

it comprises the prior steps of detecting an electrical arc, and of cutting off the power supply of the electrical system.

the modulated current applied to each of the modules is superimposed on an operating current of the electrical system.

The invention also relates to an electrical system comprising a plurality of modules that can be powered independently with current, characterised in that it further comprises:

a module for applying to each of the modules a current which is modulated by a signal specific to the module, an acoustic sensor enabling the measurement of an acoustic signal that accompanies an electrical arc generated by a defective module, a treatment unit configured to identify a signature of one of the specific signals in the acoustic signal measured by the acoustic sensor in order to identify the defective module.

BRIEF DESCRIPTION OF THE DRAWINGS

Other aspects, purposes, advantages and characteristics of the invention shall appear better when reading the following detailed description of preferred embodiments of the latter, given by way of a non-restricted example, and made in reference to the annexed drawings wherein.

DETAILED DESCRIPTION OF PARTICULAR EMBODIMENTS

The invention proposes to detect the appearance of electrical arcs in an electrical system comprising a plurality of modules that can be supplied independently with current, and more particularly to identify which of these modules is at the origin of the electrical arc.

Figure 1:
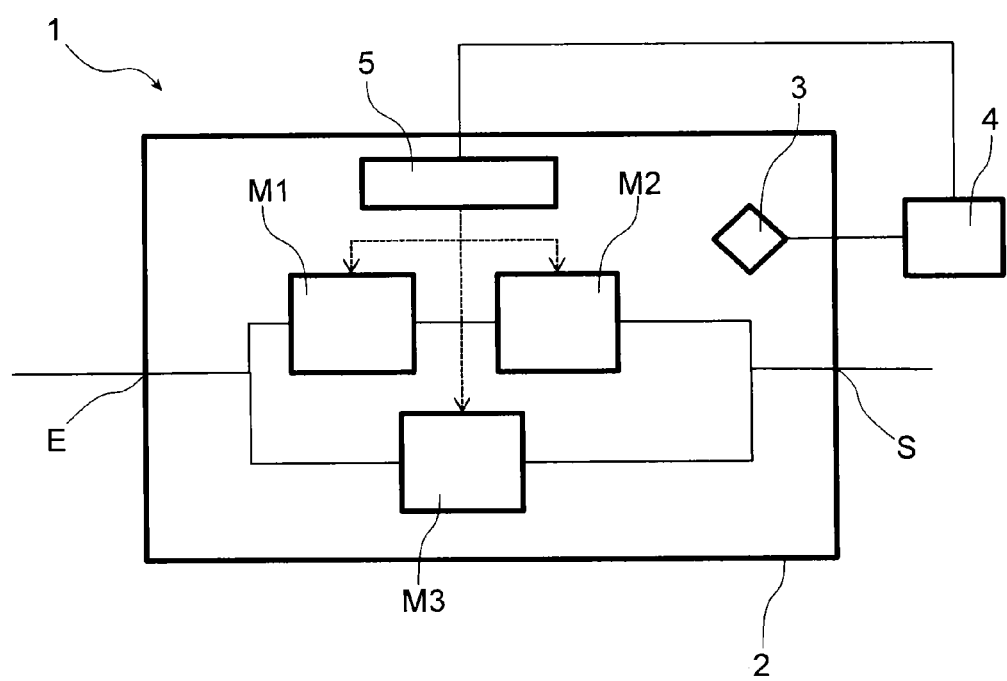
FIG. 1 is a diagram showing an example of an implementation of locating faults in an electrical system according to the invention.

FIG. 1 is a diagram showing an example of such an electrical system 1. The electrical system 1 comprises a protective case 2 inside of which are housed various sub-assemblies or modules M1-M3. By way of example purely for the purposes of information, FIG. 1 shows two modules M1 and M2 connected electrically in series between an input terminal E and an output terminal S of the electrical system 1, and a module M3 connected in parallel of the modules in series M1 and M2 between the input E and output S terminals.

An electrical arc, series or parallel, can occur when one of these modules M1-M3 is defective. This arc is accompanied by the emission of an acoustic wave.

The electrical system 1 furthermore comprises an acoustic sensor 3, for example housed in the protective case 2, which makes it possible to measure an acoustic signal that accompanies an electrical arc generated by a defective module M1-M3. The acoustic sensor 3 is for example a microphone, in particular when the medium for propagating the acoustic wave is air. It is preferentially configured for measuring ultrasounds in band between 60 and 300 kHz, more preferably between 60 and 150 kHz. The acoustic sensor 3 can have other forms, such as for example that of a piezoelectric sensor that can in particular be used to measure an acoustic signal that is propagating inside a cable.

The electrical system 1 furthermore comprises a treatment unit 4 connected to the acoustic sensor 3 in order to provide for the identifying of a defective module such as shall be detailed in what follows.

The electrical system 1 also comprises a module for applying a current 5 to each of the modules M1-M3. This module 5 is more particularly configured to apply to each of the modules a current modulated by a signal specific to the module.

Figure 2:
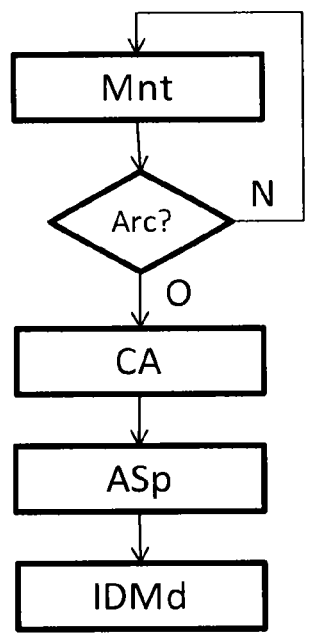
FIG. 2 is a diagram showing the steps of an example of implementing a method for locating faults in an electrical system according to the invention.

FIG. 2 shows a possible embodiment for locating faults in the electrical system 1 according to the invention and which consists in identifying the defective module at the origin of an electrical arc.

In a first step "Mnt", the occurrence of an electrical arc in the electrical system is monitored by means of an arc detector connected to the treatment unit 4 or to a dedicated treatment unit. This detector can be the acoustic sensor 3 itself, or any other type of detector such as for example an electromagnetic sensor.

When an arc generated by a defective module is detected, in a second step "CA", the power supply of the electrical system is cut off or a portion of the latter when the detection of the arc is accompanied by a locating of the latter. This cut off interrupts the electrical arc.

Then in a third step "ASp", the current is re-established at the terminals of the various modules M1-M3 of the electrical system by means of the module for applying a current 5. This module 5 more precisely applies to each of the modules M1-M3 a current which is modulated by a signal specific to the module, respectively C1-C3 for modules M1-M3. The parameters for the current modulations applied to the various modules can be supplied to the module for applying a current 5 by the treatment unit 4. On the contrary, the module for applying a current 5 can provide these modulation parameters to the treatment unit 4. However, these modulation parameters are known by constructing the module for applying a current 5 and the treatment unit 4.

Following the re-establishing of the current, the arc is then generated again on the defective module and the specific modulation of the current applied to the defective module results also in a specific modulation of the acoustic emission of the arc (a physical phenomenon known as singing arc).

In a fourth step "IDMd", the treatment unit 4 identifies a signature of one of the specific modulation signals in the acoustic signal measured by the acoustic sensor 3, and as such identifies the defective module.

Figure 3:
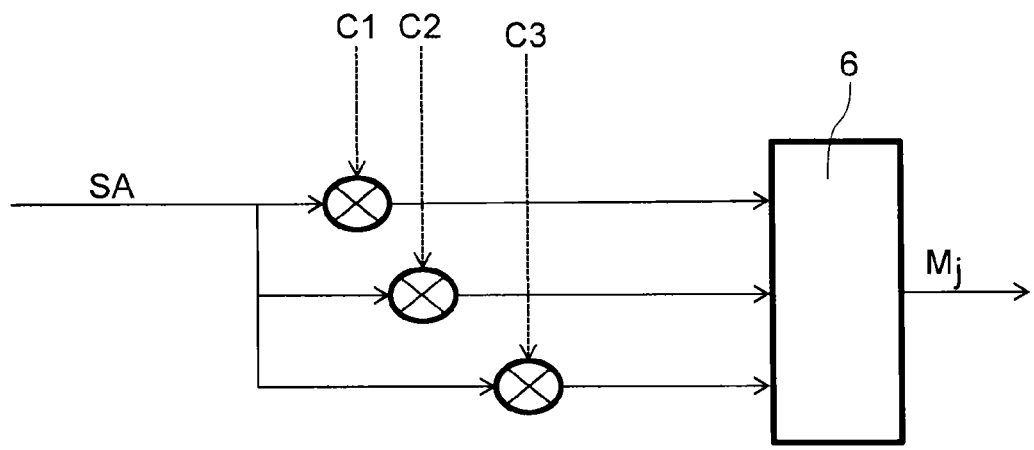
FIG. 3 is a diagram showing a possible embodiment for identifying a signature of a specific signal in the measured acoustic signal.

As shown in FIG. 3, the step of identifying "IDMd" can include a correlation of the acoustic signal SA measured by the acoustic sensor 3 with each of the specific signals C1-C3. An analysis circuit 6 of the results of the various correlations carries out a search for the auto-correlation peak from among these different results, in particular by comparing with a predetermined threshold. When such a peak is identified, the analysis circuit 6 indicates which of the modules is defective, namely the module Mj associated with the specific signal Cj modulating the acoustic signature of the electrical arc.

The search for the auto-correlation peak also allows the analysis circuit 6 to measure the propagation time of the acoustic wave from the arc generating it to the acoustic sensor 3. In a possible embodiment of the invention, there is recourse to at least three acoustic sensors 3 which makes it possible to determine the exact location of the electrical arc via a technique of triangulating the propagation times of the acoustic wave of the electrical arc to each of the acoustic sensors 4. This locating makes use of non-ambiguous measurements of propagation time and as such has the advantage of being more accurate than locating techniques that use the differences in the arrival time of the acoustic signal to each of the sensors.

As the acoustic signal SA is integrated during the correlation over the entire duration of a specific signal, a substantial gain in the treatment is provided, which significantly improves the reliability and the sensitivity of the identification of the defective module and the locating of the electrical arc.

The specific signals C1-C3 are more preferably formatted before correlation with the acoustic signal SA in order to improve the detection of the auto-correlation peak, for example by means of a waveform, in particular a rectangular waveform, thanks to which the specific signals have sharp rising and falling edges.

In another embodiment of the invention, the monitoring step "Mnt" of the occurrence of an electrical arc in the electrical system and the cut off step of the power supply "CA" following the detection of an electrical arc are not carried out. In this other embodiment, the current which is modulated by a specific signal applied to each of the modules M1-M3 is superposed on the operating current of the electrical system. The modulated current is more preferably of a lower amplitude than the operating current. The modulated current can be applied constantly, or intermittently. In this other embodiment, any electrical arc will then be detected at the same time as the identification of the defective module at the origin of the arc.

An example of a specific signal used in the invention in order to modulate a current applied to a module of the electrical system is a sequence of pseudo-random code. A Gold code or a Kasami code can also be used for example, with these codes having very good correlation properties and being able to be generated with controlled complexity.

By way of an example for the purposes of illustration, a Gold code is a pseudo-random sequence resulting from the modulo-2 sum of two sequences at maximum length (of length n) of the same period Lc and of the same rhythm. n denotes the size of the offset register, and $Lc=2^n-1$. The sum of these two sequences generates a family of codes of which the digital versions have correlation functions such that the intercorrelation $K_{C_iC_j}$ ($i \neq j$) only takes three possible values and the auto-correlation $K_{C_iC_i}$ only takes four possible values (the three values of the intercorrelations, plus one):

$$\text{for } i \neq j, K_{c_ic_j}(t) = \begin{cases} -\dfrac{1}{Lc} \\ -\dfrac{1}{Lc}t(n) \\ \dfrac{1}{Lc}[t(n)-2] \end{cases} ;$$

$$K_{c_ic_i}(t) = \begin{cases} 1 \\ -\dfrac{1}{Lc} \\ -\dfrac{1}{Lc}t(n) \\ \dfrac{1}{Lc}[t(n)-2] \end{cases} ,$$

with $$t(n) = \left[1 + 2^{\frac{n+1}{2}}\right]$$

if n is odd, and with $$t(n) = \left[1 + 2^{\frac{n+2}{2}}\right]$$

if n is even.
As such for a code of length 1023:

$$\text{for } i \neq j, K_{c_ic_j}(t) = \begin{cases} -\dfrac{1}{1023} \\ -\dfrac{65}{1023} \\ \dfrac{65}{1023} \end{cases} ;$$

$$K_{c_ic_i}(t) = \begin{cases} 1 \\ -\dfrac{1}{1023} \\ -\dfrac{65}{1023} \\ \dfrac{65}{1023} \end{cases} .$$

As such, this type of spreading code makes it possible to easily discriminate a particular code from another code, and as such identify the defective connection. The detecting of an auto-correlation peak is furthermore therefore particularly suited to the calculation of the propagation time of the acoustic wave.

The invention claimed is:

1. A method for locating faults in an electrical system comprising a plurality of modules that can be powered independently with current, the method comprising the measuring of an acoustic signal that accompanies an electrical arc generated by a defective module and further comprising the following steps:
   applying to each of the modules a respective current which is modulated by a signal specific to the module, and
   identifying a signature of one of the specific signals in the measured acoustic signal in order to identify the defective module.

2. The method according to claim 1, wherein identifying the signature of one of the specific signals in the measured acoustic signal comprises calculating a correlation of the measured acoustic signal with each one of the specific signals.

3. The method according to claim 2, wherein identifying the defective module comprises the identification of an auto-correlation peak from among the correlation results of the measured acoustic signal with each one of the specific signals.

4. The method according to claim 2, further comprising a step of locating the electrical arc by determining, using the auto-correlation results of the measured acoustic signal with the specific signal associated with the defective module, the propagation time of the acoustic wave from the electrical arc to an acoustic sensor taking the measurement of the acoustic signal.

5. The method according to claim 4, comprising determining the propagation time of the acoustic wave from the electrical arc to at least three acoustic sensors taking the measurement of the acoustic signal, and triangulating of the determined propagation times.

6. The method according to claim 1, wherein a signal specific to a module is a sequence of pseudo-random code, for example a Gold code or a Kasami code.

7. The method according to claim 2, wherein each of the specific signals is formatted by a rectangular waveform before correlation with the acoustic signal measured.

8. The method according to claim 1, comprising the prior steps of detecting an electrical arc, and of cutting off the power of the electrical system.

9. The method according to claim 1, wherein the modulated current applied to each of the modules is superimposed with an operating current of the electrical system.

10. An electrical system comprising a plurality of modules that can be powered independently with current and an acoustic sensor enabling the measurement of an acoustic signal that accompanies an electrical arc generated by a defective module, wherein the system further comprises:
   a current application module configured to apply to each of the plurality of modules a respective current which is modulated by a signal specific to the module, and
   a treatment unit configured to identify a signature of one of the specific signals in the acoustic signal measured by the acoustic sensor in order to identify the defective module.

* * * * *